United States Patent [19]

Cavender et al.

[11] 4,304,779

[45] Dec. 8, 1981

[54] 6-(NITROGEN-CONTAINING HETEROCYCLIC)HYDROXYMETHYL-PENICILLANIC ACIDS, COMPOUNDS RELATED THERETO AND PROCESSES FOR THEIR PREPARATION

[75] Inventors: Patricia L. Cavender, Cranbury; Ashit K. Ganguly, Upper Montclair; Viyyoor M. Girijavallabhan, Bloomfield, all of N.J.

[73] Assignee: Schering Corporation, Kenilworth, N.J.

[21] Appl. No.: 37,263

[22] Filed: May 9, 1979

[51] Int. Cl.$^3$ .............................................. C07D 499/00
[52] U.S. Cl. .............................. 424/258; 260/24.52 R; 260/326.15; 424/270; 424/274; 424/275; 424/263; 546/152; 546/273

[58] Field of Search ........... 260/326.16, 245.2, 326.15; 424/263, 270, 274, 275, 258; 546/152, 273

[56] References Cited

U.S. PATENT DOCUMENTS 4,207,323  6/1980  Beattie et al. ...................... 424/270

Primary Examiner—Nicholas S. Rizzo
Attorney, Agent, or Firm—Mary S. King; Barbara L. Renda

[57] ABSTRACT

6-(Heterocyclic)hydroxymethylpenicillanic acids and compounds related thereto are prepared by reaction of a 6,6-dihalopenicillanic acid with a Grignard reagent and a heterocyclic aldehyde in an anhydrous aprotic solvent. The compounds possess useful antibacterial activity.

18 Claims, No Drawings

6-(NITROGEN-CONTAINING HETEROCYCLIC)HYDROXYMETHYLPENICIL- LANIC ACIDS, COMPOUNDS RELATED THERETO AND PROCESSES FOR THEIR PREPARATION

The present invention relates to 6-(nitrogen-containing heterocyclic)hydroxymethylpenicillanic acids, compounds related thereto and processes for their preparation. More particularly, the compound aspect of this invention relates to compounds of the formula

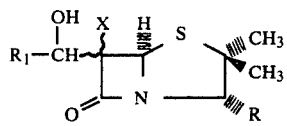

wherein
R is —COOH, —COOR$_2$, —COO alkali metal, —CN, or a tetrazol-5-yl group;
R$_1$ is a nitrogen-containing heterocyclic group;
R$_2$ is lower alkyl, allyl or aralkyl;
X is hydrogen, bromo, chloro or iodo; and the wavy lines denote the alternate α and β stereochemical configurations.

The asymmetric carbon atom present in the 6-substituent of the compounds results in both R and S forms and mixtures thereof. The present invention encompasses both the unresolved RS mixtures and the resolved pure R or S isomers.

The term "nitrogen-containing heterocyclic" as used herein refers to 4–10 membered heterocyclic rings having one or more nitrogen atoms therein. Representative are those such as pyridyl, quinolinyl, pyrrolyl and indolyl, optionally substituted by one or more lower alkyl groups. Also encompassed by this term are the multiple position isomers, e.g., 3-pyridyl, 4-pyridyl, etc.

The lower alkyl groups referred to above contain 1 to 6 carbon atoms and are exemplified by methyl, ethyl, propyl, butyl, pentyl, hexyl, and the corresponding branched-chain isomers thereof.

The term "aralkyl" as used herein refers to lower alkyl groups substituted by one or more phenyl or lower alkyl- or lower alkoxy - phenyl groups.

The term "allyl" refers to allylic groups derived from common allylic alcohols such as allyl alcohol, crotyl alcohol and cinnamyl alcohol.

The lower alkoxy groups referred to above likewise contain 1–6 carbon atoms and are exemplified by methoxy, ethoxy, propoxy and the like.

The alkali metal cations referred to above preferably are potassium and sodium but may also be lithium, rubidium or cesium.

The wavy lines are used herein to denote the alternate α or β stereochemical configuration. The α substituent lies behind the plane of the β-lactam ring, while a βsubstituent lies above it. Natural penicillins have the 6β-configuration which may be represented as follows

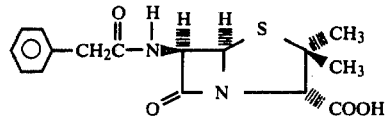

A particularly preferred group of compounds encompassed by this invention are those of the formula

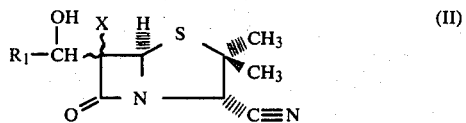

wherein X, R$_1$ and the wavy lines are as hereinbefore defined.

The compounds of this invention possess antibacterial activity of both the gram-positive and gram-negative type. Thus, when tested in standardized microbiological assays, the compounds of this invention are active vis-a-vis such gram-positive organisms as *Staphylococcus epidermidis*, *Salmonella*, and *Bacillus subtilis*, at test levels of 0.1 to 100 μg/ml. Additionally, they show activity against such organisms in the presence of penicillinase and cephalosporinase indicating resistance to these enzymes. For instance, 6β-[(3-pyridyl)-hydroxymethyl]2,2-dimethyl-3α-cyanopenam is active vis-a-vis *Staph. aureus* at a test level of 2–8 μg/ml and *B. subtilis* at a test level of 8–32 μg/ml.

Thus, the present invention includes within its scope pharmaceutical compositions comprising an antibacterially effective amount of a compound of formula I together with a compatible, pharmaceutically acceptable carrier or coating. Also included within this invention is the method of eliciting an antibacterial response in a warm-blooded animal having a susceptible bacterial infection which comprises administering to said animal a non-toxic, antibacterially effective amount of a compound of formula I.

The dosage administered of the compounds of this invention is dependent upon the age and weight of the animal species being treated, the mode of administration, and the type and severity of bacterial infection being prevented or reduced. Typically, the dosage administered per day will be in the range of 100–5000 mg, with 500–1000 mg being preferred.

For oral administration, the compounds of this invention may be formulated in the form of tablets, capsules, elixirs or the like. Likewise, they may be admixed with animal feed. They may also be applied topically in the form of ointments, both hydrophilic and hydrophobic, in the form of lotions which may be aqueous, non-aqueous or of the emulsion type, or in the form of creams.

The compounds of formula I may be utilized in liquid form such as solutions, suspensions, creams and the like for oral, otic, optic and topical use and may also be administered parenterally, preferably via intramuscular or intravenous injection.

The process aspect of this invention involves the preparation of compounds of the formula

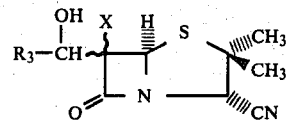

wherein R$_3$ is a heterocyclic group containing one or more nitrogen, sulfur or oxygen atoms and X is bromo, chloro or iodo via a novel reaction sequence which comprises reacting a 6,6-dihalopenam of the formula

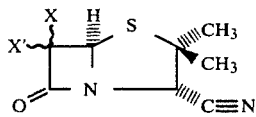

(III)

wherein X and X' are independently chloro, bromo or iodo, and the wavy lines are as hereinbefore defined, with a suitable Grignard reagent and a nitrogen sulfur or oxygen containing heterocyclic aldehyde of the formula

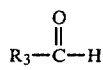

wherein $R_3$ is as hereinbefore defined, in an anhydrous aprotic solvent at a temperature of $-78°$ to $0°$ C.

Although Grignard reactions are well-known, it is surprising that the reaction would preferentially occur at the 6-position rather than at the 3-cyano substituent. As such, this novel reaction comprises a process aspect of our invention, which, contrary to other substitution methods, affords the production of a 6-substituted compound. Other methods, such as utilizing n-butyl lithium, afford mixtures of des-bromo starting material and ring-opened degradation products rather than the desired 6-substituted compounds. We have additionally discovered that other synthetic methods, e.g., the zinc reaction disclosed in copending U.S. Ser. No. 911,858, filed June 2, 1978 by Viyyoor M. Girijavallabhan, et al. entitled "Novel Synthesis of β-Lactams Having a Substituted Hydroxymethylene Group at the Position Alpha to the Lactam Carbonyl Group" will not afford the 3-cyano-nitrogen-containing heterocyclic compounds of this invention due to competing side-reactions. Thus, the process of the present invention affords the only workable route to such 3-cyano compounds. This process has additionally been found to be useful for the preparation of other heterocyclic-substituted compounds, e.g., compounds wherein the heterocyclic group contains one or more oxygen and sulfur atoms such as furanyl or thienyl.

The X and X' may be alike or different depending upon the desired final X substituent and the reactivity of the particular Grignard reagent. When the desired X substituent is bromo, then a 6,6-dibromo starting material would be utilized. When the desired X substituent is chloro, a 6-chloro-6-bromo starting material is preferred since the Grignard will preferably react with the 6-bromo and give the 6-(heterocyclic)hydroxymethyl substituent in its place and leave the 6-chloro intact. When the 6-iodo X substituent is desired a 6,6-diiodo substituent on the starting compound is preferred.

The reaction is conducted in an anhydrous aprotic solvent such as ethyl ether, diglyme or tetrahydrofuran. Preferred temperatures are $-78°$ to $0°$ C. in order to minimize side reactions. Typical reaction times are in the range of 0.5 to 5 hours, depending upon the nature of the reactant.

The compounds of formula I wherein X is hydrogen, and R is cyano are prepared from the corresponding 6-bromo compound by treatment with a dehalogenating agent such as tri-n-butyltin hydride. Typically, an anhydrous aprotic solvent such as ethyl ether or tetrahydrofuran is used. Typical reaction times are 1–12 hours and typical reaction temperatures are 10°–50° C. Most typically, room temperature is utilized.

The compounds of formula I wherein X is chloro, bromo or iodo and R is $-COOR_2$ are prepared in a manner similar to the 3-cyano compounds, i.e., by reaction of a compound of the formula

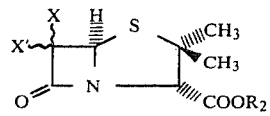

(IV)

wherein $R_2$, X, X' and the wavy lines are as hereinbefore defined, with a Grignard reagent and a heterocyclic aldehyde of the formula V

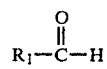

(V)

wherein $R_1$ is as hereinbefore defined. The compounds of formula I wherein X is hydrogen and R is $-COOR_2$ may then be prepared from the corresponding 6-bromo compounds as detailed for the 3-cyano compounds.

Alternatively, and preferably, however, the compounds of formula I wherein R is $-COOR_2$ and X is hydrogen are prepared by reacting a compound of the formula

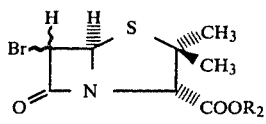

(VI)

wherein $R_2$ and the wavy lines are as hereinbefore defined, with n-butyllithium in an anhydrous aprotic solvent at temperatures of $-78°$ to $0°$ C., followed by addition of the appropriate heterocyclic aldehyde of formula V.

Removal of the esterifying function of the compounds of formula I wherein R is $-COOR_2$ and $R_2$ is lower alkyl, allyl or aralkyl affords the compounds wherein R is $-COOH$ (the free acids). Depending on the nature of the $R_2$ group, this is typically accomplished by acid hydrolysis treatment with an acid such as trifluoro acetic acid or, alternatively, hydrogenation using a palladium or palladium-on-carbon catalyst. The allyl groups are preferably removed by use of a palladium catalyst with 2-ethylhexanoic acid or a salt thereof according to the procedure of McCombie described in copending U.S. Ser. No. 002,472, filed Jan. 10, 1979, of common assignee as the instant application. The alkali metal salts may then be prepared by treating the $-COOH$ compounds with an alkali metal carbonate solution, e.g., potassium or sodium carbonate.

The compounds of formula I wherein R is a tetrazol-5-yl group are prepared from the corresponding compounds wherein X is cyano according to the procedures described in U.S. Pat. No. 3,992,394.

The 6,6-dihalo starting materials of formulae III and IV are prepared by reaction of the corresponding 6-diazo compound with bromine according to the procedure of DiNinno, et al., *J. Org. Chem.*, 42, 2960 (1977). Alternatively by the procedure of Clayton, *J.C.S.(C)*, 2123 (1969), the 6-amino compound can be converted to separable mixtures of the mono or di-halo starting compounds. Other methods of preparation are also found in Flynn, "Cephalosporins and Penicillins", Chapter 3 (1972).

The 3α-nitrile-substituted compounds may be produced from the corresponding acids by first converting to the amide and then to the nitrile. Methods for these processes are found in U.S. Pat. No. 3,992,394.

The pure R or S isomers are obtainable by conventional resolution methods beginning with the RS mixture prepared by the above-described procedures or by beginning with starting materials derived from a natural penicillin. Typically, a salt is formed with an optically active resolving agent with successive fractional crystallizations affording the pure isomers.

Representative compounds of this invention preparable by the above reaction sequences include the following:

6β-bromo-6α-[(3-pyridyl)hydroxymethyl]-2,2-dimethyl-3α-cyanopenam;
6β-chloro-6α-[(3-pyridyl)hydroxymethyl]-2,2-dimethyl-3α-cyanopenam;
6β-iodo-6α-[(3-pyridyl)hydroxymethyl]-2,2-dimethyl-3α-cyanopenam;
6β-[(3-pyridyl)hydroxymethyl]-2,2-dimethyl-3α-cyanopenam;
6α-[(3-pyridyl)hydroxymethyl]-2,2-dimethyl-3α-cyanopenam;
6β-bromo-6α-[(3-quinolinyl)hydroxymethyl]-2,2-dimethyl-3α-cyanopenam;
6β-bromo-6α-[(4-pyridyl)hydroxymethyl]-2,2-dimethyl-3α-cyanopenam;
6β-bromo-6α-[(2-indolyl)hydroxymethyl]-2,2-dimethyl-3α-cyanopenam;
6β-bromo-6α-[(1-methyl-2-pyrrolyl)hydroxymethyl]-2,2-dimethyl-3α-cyanopenam;
6β-[(3-quinolinyl)hydroxymethyl]-2,2-dimethyl-3α-cyanopenam;
6α-[(3-quinolinyl)hydroxymethyl]-2,2-dimethyl-3α-cyanopenam;
6β-[(4-pyridyl)hydroxymethyl]-2,2-dimethyl-3α-cyanopenam;
6α-[(4-pyridyl)hydroxymethyl]-2,2-dimethyl-3α-cyanopenam;
6β-[(2-indolyl)hydroxymethyl]-2,2-dimethyl-3α-cyanopenam;
6α-(2-indolyl)hydroxymethyl]-2,2-dimethyl-3α-cyanopenam;
6β-[(1-methyl-2-pyrrolyl)hydroxymethyl]-2,2-dimethyl-3α-cyanopenam;
6α-[(1-methyl-2-pyrrolyl)hydroxymethyl]2,2-dimethyl-3α-cyanopenam;
6β-[(3-pyridyl)hydroxymethyl]-2,2-dimethyl-3α-(tetrazol-5-yl)-penam;
6α-[(3-pyridyl)hydroxymethyl]-2,2-dimethyl-3α-(tetrazol-5-yl)-penam;
6β-[(4-pyridyl)hydroxymethyl]-2,2-dimethyl-3α-(tetrazol-5-yl)-penam;
6α-[(4-pyridyl)hydroxymethyl]-2,2-dimethyl-3α-(tetrazol-5-yl)-penam;
benzhydryl 6β-bromo-6α-[(3-pyridyl)hydroxymethyl]penicillanate;
benzyl 6β-bromo-6α-[(3-pyridyl)hydroxymethyl]penicillanate;
methyl 6β-bromo-6α-[(3-pyridyl)hydroxymethyl]penicillanate;
t-butyl 6β-bromo-6α-[(3-pyridyl)hydroxymethyl]penicillanate;
sodium 6β-bromo-6α-[(3-pyridyl)hydroxymethyl]penicillanate;
potassium 6β-bromo-6α-[(3-pyridyl)hydroxymethyl]penicillanate;
benzhydryl 6β-[(3-pyridyl)hydroxymethyl]penicillanate;
benzyl 6β-[(3-pyridyl)hydroxymethyl]penicillanate;
methyl 6β-[(3-pyridyl)hydroxymethyl]penicillanate;
t-butyl 6β-[(3-pyridyl)hydroxymethyl]penicillanate;
sodium 6β-[(3-pyridyl)hydroxymethyl]penicillanate;
potassium 6β-[(3-pyridyl)hydroxymethyl]penicillanate;
benzhydryl 6α-[(3-pyridyl)hydroxymethyl]penicillanate;
benzyl 6α-[(3-pyridyl)hydroxymethyl]penicillanate;
methyl 6α-[(3-pyridyl)hydroxymethyl]penicillanate;
t-butyl 6α-[(3-pyridyl)hydroxymethyl]penicillanate;
sodium 6α-[(3-pyridyl)hydroxymethyl]penicillanate;
potassium 6α-[(3-pyridyl)hydroxymethyl]penicillanate;
6α-[(3-pyridyl)hydroxymethyl]penicillanic acid;
6α-[(2-indolyl)hydroxymethyl]penicillanic acid;
6α-[(4-pyridyl)hydroxymethyl]penicillanic acid;
6α-[(1-methyl-2-pyrrolyl)hydroxymethyl]penicillanic acid;
6α-[(3-quinolinyl)hydroxymethyl]penicillanic acid;
6β-[(3-pyridyl)hydroxymethyl]penicillanic acid;
6β-[(2-pyridyl)hydroxymethyl]penicillanic acid;
6β-[(4-pyridyl)hydroxymethyl]penicillanic acid;
6β-[(1-methyl-2-pyrrolyl)hydroxymethyl]penicillanic acid; and
6β-[(3-quinolinyl)hydroxymethyl]penicillanic acid.

The following compounds may be prepared also by the process of this invention:

6β-bromo-6α-[(2-thienyl)hydroxymethyl]-2,2-dimethyl-3α-cyanopenam;
6β-bromo-6α-[(2-furanyl)hydroxymethyl]-2,2-dimethyl-3α-cyanopenam;
6β-[(2-thienyl)hydroxymethyl]-2,2-dimethyl-3α-cyanopenam;
6α-[(2-thienyl)hydroxymethyl]-2,2-dimethyl-3α-cyanopenam;
6β-[(2-furanyl)hydroxymethyl]-2,2-dimethyl-3α-cyanopenam;
6α[(2-furanyl)hydroxymethyl]-2,2-dimethyl-3α-cyanopenam;
6β-[(2-furanyl)hydroxymethyl]-2,2-dimethyl-3α-(tetrazol-5-yl)-penam;
6α-[(2-furanyl)hydroxymethyl]-2,2-dimethyl-3α-(tetrazol-5-yl)-penam;
6α[(2-furanyl)hydroxymethyl]penicillanic acid;
6α-[(2-thienyl)hydroxymethyl]penicillanic acid;
6β-[(2-furanyl)hydroxymethyl]penicillanic acid; and
6β-[(2-thienyl)hydroxymethyl]penicillanic acid.

The following examples describe in detail the process of the present invention and the compounds produced therefrom. It will be apparent to those skilled in the art that many modifications, both of materials and methods, may be practiced without departing from the spirit and scope of the invention.

EXAMPLE 1

A. A solution of methyl magnesium bromide in ether (0.2 ml, 3M, 0.6 mmol) is added to a solution of 6,6-dibromo-3α-cyano-2,2-dimethylpenam (170 mg, 0.5 mmol) in 5 ml of tetrahydrofuran at −78° C. After 20 minutes, a solution of 3-pyridinecarboxaldehyde (0.1 ml, 1 mmol) in 1 ml of tetrahydrofuran is added. After an additional twenty minutes, a saturated solution of potassium dihydrogen phosphate (pH 3, 0.2 ml) is added. The reaction mixture is allowed to warm to room temperature and then is diluted with ethyl acetate. The solids are removed by filtration and the filtrate washed with saturated sodium chloride. Drying over anhydrous sodium sulfate, filtration and evaporation of the solvents affords solid material which, after purification by PLC (preparative thin layer chromatography), gives 6β-bromo-6α-[(3-pyridyl)hydroxymethyl]-2,2-dimethyl-3α-cyanopenam.

The assigned stereochemistry is confirmed by single crystal x-ray analysis.

B. 6β-bromo-6α-[(3-pyridyl)hydroxymethyl]-2,2-dimethyl-3α-cyanopenam (0.55 g, 1.5 mmol) is dissolved in 0.5 ml of tetrahydrofuran and 0.22 ml (1.1 eq) of freshly distilled tri-n-butyltin hydride (70°/0.4 mm) is added. After stirring for three hours at room temperature, the reaction mixture is refrigerated overnight. Solvent removal and repeated recrystallization from acetone/hexane affords 6β-[(3-pyridyl)hydroxymethyl]-2,2-dimethyl-3α-cyanopenam. This product has nuclear magnetic resonance peaks at δ=1.70(s), 1.76(s), 4.18(dd), 5.03(s), 5.28(m), 5.60(d), 7.45(m), 7.85(m) and 8.55(m). Alternatively PLC (35% acetone/toluene; 2 developments) of the reaction mixture provides recovered starting material and product in a 3:7 ratio.

EXAMPLE 2

Benzhydryl 6α-bromopenicillanate (3.0 g, 6.7 mmol) is dissolved in 30 ml of ether and 0.5 ml of tetrahydrofuran and cooled to −78° C. A solution of 2.2M n-butyllithium in hexane (1.8 ml, 4 mmol) is added and allowed to stir for 2 minutes. A solution of 7 ml of 3-pyridinecarboxaldehyde in 5 ml of ether is then added all at once to the solution. After stirring for 15 minutes, 2 ml of a saturated potassium dihydrogen phosphate solution is added and the reaction warmed to room temperature. The solids are dissolved in water and the layers separated. The aqueous solution is extracted one with ethyl acetate. The combined organic solutions are then washed with saturated sodium chloride, dried (anhydrous sodium sulfate) and evaporated to give a mixture of benzhydryl 6α-bromopenicillanate, 3-pyridinecarboxaldehyde and benzhydryl 6α-[(3-pyridyl)hydroxymethyl]-penicillanate.

Rapid chromatography on silica gel eluting first with chloroform and then with 10% acetone in chloroform affords pure benzhydryl 6α-[(3-pyridyl)hydroxymethyl]penicillanate.

EXAMPLE 3

Repetition of the procedure detailed in Example 1A using benzhydryl 6,6-dibromopenicillanate affords benzhydryl 6β-bromo-6α-[(3-pyridyl)hydroxymethyl]-penicillanate.

Reduction of benzhydryl 6β-bromo-6α-[(3-pyridyl)-hydroxymethyl]penicillanate with tri-n-butyltin hydride according to the procedure of Example 1B provides benzhydryl 6β-[(3-pyridyl)hydroxymethyl]-penicillanate.

EXAMPLE 4

Benzhydryl 6β-[(3-pyridyl)hydroxymethyl]penicillanate and benzhydryl 6α-[(3-pyridyl)hydroxymethyl]-penicillanate are treated with trifluoroacetic acid/anisole (3:2 v/v) at 5° C. for 5 minutes. The reagents are removed under high vacuum. The residue is then taken up in a small amount of acetone and triturated with hexane to give 6β-[(3-pyridyl)hydroxymethyl]-penicillanic acid and 6α-[(3-pyridyl)hydroxymethyl]-penicillanic acid, respectively.

What is claimed is:

1. A compound of the formula

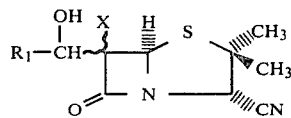

wherein

R₁ is a nitrogen-containing heterocyclic group selected from the group consisting of pyridyl, quinolinyl, pyrrolyl, indolyl, lower alkyl derivatives thereof;

X is hydrogen, bromo, chloro or iodo; and the wavy lines denote the alternate α and β sterechemical configurations.

2. A compound according to claim 1 wherein X is hydrogen or bromo.

3. A compound according to claim 1 wherein R₁ is a pyridyl group.

4. A compound according to claim 1 wherein R₁ is a 1-methyl-2-pyrrolyl group.

5. A compound according to claim 1 wherein R₁ is a quinolinyl group.

6. A compound according to claim 3 which is 6β-bromo-6α-[(3-pyridyl)hydroxymethyl]-2,2-dimethyl-3α-cyanopenam.

7. A compound according to claim 3 which is 6β-[(3-pyridyl)hydroxymethyl]-2,2-dimethyl-3α-cyanopenam.

8. A compound according to claim 3 which is 6β-bromo-6α-[(4-pyridyl)hydroxymethyl]-2,2-dimethyl-3α-cyanopenam.

9. A compound according to claim 3 which is 6β-[(4-pyridyl)hydroxymethyl]-2,2-dimethyl-3α-cyanopenam.

10. A compound according to claim 4 which is 6β-bromo-6α-[(1-methyl-2-pyrrolyl)hydroxymethyl]-2,2-dimethyl-3α-cyanopenam.

11. A compound according to claim 4 which is 6β-[(1-methyl-2-pyrrolyl)hydroxymethyl]-2,2-dimethyl-3α-cyanopenam.

12. A compound according to claim 4 which is 6α-[(1-methyl-2-pyrrolyl)hydroxymethyl]-2,2-dimethyl-3α-cyanopenam.

13. A compound according to claim 5 which is 6β-bromo-6α-[(3-quinolinyl)hydroxymethyl]-2,2-dimethyl-3α-cyanopenam.

14. A compound according to claim 5 which is 6β-[(3-quinolinyl)hydroxymethyl]-2,2-dimethyl-3α-cyanopenam.

15. A compound according to claim 5 which is 6α-[(3-quinolinyl)hydroxymethyl]-2,2-dimethyl-3α-cyanopenam.

16. A pharmaceutical composition comprising an antibacterially effective amount of a compound of claim 1 together with a non-toxic pharmaceutically acceptable carrier.

17. The method of eliciting an antibacterial response in a warm-blooded animal having a susceptible bacterial infection which comprises administering to said animal a non-toxic, antibacterially effective amount of a compound of claim 1.

18. A process for preparing compounds of the formula

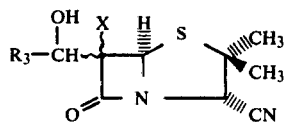

wherein
R₃ is a heterocyclic group containing one or more nitrogen, sulfur or oxygen atoms selected from the group consisting of pyridyl, quinolinyl, pyrrolyl, indolyl, thienyl, furanyl, and lower alkyl derivatives thereof;

X is hydrogen, bromo, chloro or iodo; and the wavy lines denote the alternate α and β stereochemical configurations;

which comprises reacting a 6,6-dihalopenam of the formula

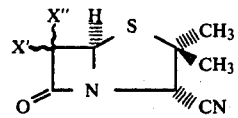

wherein X' and X" are independently chloro, bromo or iodo, with a Grignard reagent and a heterocyclic aldehyde of the formula

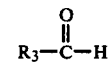

wherein R₃ is as hereinabove defined in an anhydrous aprotic solvent at temperatures of −78° to 0° C.

* * * * *